US011318264B2

(12) United States Patent
Yilmaz

(10) Patent No.: US 11,318,264 B2
(45) Date of Patent: May 3, 2022

(54) AEROSOL GENERATING DEVICE AND ARTICLE

(71) Applicant: BRITISH AMERICAN TOBACCO (INVESTMENTS) LIMITED, London (GB)

(72) Inventor: Ugurhan Yilmaz, London (GB)

(73) Assignee: Nicoventures Trading Limited, London (GB)

( * ) Notice: Subject to any disclaimer, the term of this patent is extended or adjusted under 35 U.S.C. 154(b) by 231 days.

(21) Appl. No.: 16/475,586

(22) PCT Filed: Dec. 20, 2017

(86) PCT No.: PCT/EP2017/083785
§ 371 (c)(1),
(2) Date: Jul. 2, 2019

(87) PCT Pub. No.: WO2018/130391
PCT Pub. Date: Jul. 19, 2018

(65) Prior Publication Data
US 2019/0343182 A1    Nov. 14, 2019

(30) Foreign Application Priority Data
Jan. 13, 2017 (GB) ...................... 1700620

(51) Int. Cl.
*A24F 13/00*  (2006.01)
*A61M 15/06*  (2006.01)
(Continued)

(52) U.S. Cl.
CPC ............ *A61M 15/06* (2013.01); *A24D 1/20* (2020.01); *A24F 7/00* (2013.01); *A24F 40/46* (2020.01);
(Continued)

(58) Field of Classification Search
CPC ....................................................... A24F 47/00
(Continued)

(56) References Cited

U.S. PATENT DOCUMENTS 2,153,623 A    4/1939 Jacobson
2,956,568 A    10/1960 Magnus et al.
(Continued)

FOREIGN PATENT DOCUMENTS

AR    089648 A1    9/2014
AR    091949 A1    3/2015
(Continued)

OTHER PUBLICATIONS

International Search Report and Written Opinion, Application No. PCT/EP2017/083785, dated Apr. 9, 2018, 14 pages.
(Continued)

*Primary Examiner* — Phuong K Dinh
(74) *Attorney, Agent, or Firm* — Patterson Thuente Pedersen, P.A.

(57) ABSTRACT

An aerosol generating device defines a first flow path from an air inlet to an outlet, and a second, separate flow path from the (or another) air inlet to the outlet. The device includes a container for aerosol generating material, a heating element arranged to heat the material to generate, in the first flow path, a flow of aerosol; and the (or another) heating element arranged to heat inlet air from the air inlet or the other air inlet to generate, in the second flow path, a flow of heated air. A receiving portion, in the second flow path, is arranged to receive an element for modifying a property of the flow of heated air, thereby to generate, in the second flow path, a flow of modified air. Also disclosed is an aerosol generating device and article wherein first and second flow paths extend substantially parallel to one another.

20 Claims, 3 Drawing Sheets

(51) Int. Cl.
    *A24F 7/00*         (2006.01)
    *H05B 3/44*        (2006.01)
    *A24D 1/20*        (2020.01)
    *A24F 40/46*      (2020.01)
    *A24F 40/485*     (2020.01)
    *A24F 40/10*      (2020.01)

(52) U.S. Cl.
    CPC ............. *A24F 40/485* (2020.01); *H05B 3/44* (2013.01); *A24F 40/10* (2020.01)

(58) Field of Classification Search
    USPC .................................................. 131/328–329
    See application file for complete search history.

(56) References Cited

U.S. PATENT DOCUMENTS

| | | |
|---|---|---|
| 3,339,557 A | 9/1967 | Karalus |
| 3,468,316 A | 9/1969 | Baum et al. |
| 4,038,994 A | 8/1977 | Aikman |
| 4,227,540 A | 10/1980 | Edison |
| 4,338,931 A | 7/1982 | Cavazza |
| 4,478,228 A | 10/1984 | Chister |
| 4,484,590 A | 11/1984 | Singh |
| 4,559,955 A | 12/1985 | Brockway et al. |
| 4,637,407 A | 1/1987 | Bonanno et al. |
| 4,677,995 A | 7/1987 | Kallianos et al. |
| 4,848,375 A | 7/1989 | Patron et al. |
| 4,945,931 A | 8/1990 | Gori |
| 4,991,605 A | 2/1991 | Keritsis |
| 5,060,671 A | 10/1991 | Counts |
| 5,095,921 A | 3/1992 | Losee |
| 5,105,831 A | 4/1992 | Banerjee |
| 5,322,075 A | 6/1994 | Deevi et al. |
| 5,408,574 A | 4/1995 | Deevi et al. |
| 5,468,936 A | 11/1995 | Deevi et al. |
| 5,573,692 A | 11/1996 | Das et al. |
| 5,819,756 A | 10/1998 | Mielordt |
| 5,865,186 A | 2/1999 | Volsey |
| 5,878,752 A | 3/1999 | Adams et al. |
| 6,336,896 B1 | 1/2002 | Hsu et al. |
| 6,382,465 B1 | 5/2002 | Greiner-Perth |
| 6,606,992 B1 | 8/2003 | Schuler et al. |
| 6,705,313 B2 | 3/2004 | Niccolai |
| 6,708,846 B1 | 3/2004 | Fuchs et al. |
| 7,374,063 B2 | 5/2008 | Reid |
| 7,658,197 B1 | 2/2010 | Villagomez |
| 8,377,009 B2 | 2/2013 | Sullivan et al. |
| 8,997,753 B2 | 4/2015 | Li et al. |
| 8,997,754 B2 | 4/2015 | Tucker et al. |
| 9,004,073 B2 | 4/2015 | Tucker et al. |
| 9,247,773 B2 | 2/2016 | Memari et al. |
| 9,282,772 B2 | 3/2016 | Tucker et al. |
| 9,693,587 B2 | 7/2017 | Plojoux et al. |
| 10,010,687 B2 | 7/2018 | Von Schuckmann |
| 10,426,199 B2 | 10/2019 | Turner et al. |
| 10,470,491 B2 | 11/2019 | Sutton et al. |
| 10,492,526 B2 | 12/2019 | Sampson et al. |
| 10,758,686 B2 | 9/2020 | Reevell |
| 2002/0079377 A1 | 6/2002 | Nichols |
| 2003/0183616 A1 | 10/2003 | Goto |
| 2004/0237974 A1 | 12/2004 | Min |
| 2005/0000518 A1 | 1/2005 | Dunkley et al. |
| 2005/0016533 A1 | 1/2005 | Schuler et al. |
| 2005/0022813 A1 | 2/2005 | Alston |
| 2005/0048003 A1 | 3/2005 | Ohki et al. |
| 2005/0056280 A1 | 3/2005 | Alston et al. |
| 2005/0081852 A1 | 4/2005 | Rangachari |
| 2005/0126568 A1 | 6/2005 | Davies et al. |
| 2005/0150492 A1 | 7/2005 | Dunkley et al. |
| 2006/0272659 A1 | 12/2006 | Kobal et al. |
| 2007/0012327 A1 | 1/2007 | Karles et al. |
| 2008/0053465 A1 | 3/2008 | Tarora et al. |
| 2008/0092912 A1 | 4/2008 | Robinson |
| 2010/0200006 A1 | 8/2010 | Robinson et al. |
| 2011/0126848 A1 | 6/2011 | Zuber et al. |
| 2013/0037041 A1 | 2/2013 | Worm et al. |
| 2013/0037042 A1 | 2/2013 | Hearn et al. |
| 2013/0042865 A1 | 2/2013 | Monsees et al. |
| 2013/0068081 A1 | 3/2013 | Kronberg et al. |
| 2013/0192615 A1 | 8/2013 | Tucker et al. |
| 2013/0192616 A1 | 8/2013 | Tucker et al. |
| 2013/0192619 A1 | 8/2013 | Tucker et al. |
| 2013/0192620 A1 | 8/2013 | Tucker et al. |
| 2013/0192621 A1 | 8/2013 | Li et al. |
| 2013/0192622 A1 | 8/2013 | Tucker et al. |
| 2013/0192623 A1 | 8/2013 | Tucker et al. |
| 2013/0298905 A1 | 11/2013 | Levin et al. |
| 2013/0312742 A1 | 11/2013 | Monsees et al. |
| 2013/0333709 A1 | 12/2013 | Shimizu |
| 2014/0060556 A1* | 3/2014 | Liu .................. A24F 40/30 131/329 |
| 2014/0202479 A1 | 7/2014 | Nicholls et al. |
| 2014/0209105 A1 | 7/2014 | Sears et al. |
| 2014/0366898 A1 | 12/2014 | Monsees |
| 2015/0027469 A1 | 1/2015 | Tucker et al. |
| 2015/0027477 A1 | 1/2015 | Yoshino et al. |
| 2015/0245654 A1 | 9/2015 | Memari et al. |
| 2015/0245655 A1 | 9/2015 | Memari et al. |
| 2015/0245656 A1 | 9/2015 | Memari et al. |
| 2015/0245657 A1 | 9/2015 | Memari et al. |
| 2015/0245662 A1 | 9/2015 | Memari et al. |
| 2015/0245663 A1 | 9/2015 | Memari et al. |
| 2015/0245664 A1 | 9/2015 | Memari et al. |
| 2015/0245665 A1 | 9/2015 | Memari et al. |
| 2015/0245666 A1 | 9/2015 | Memari et al. |
| 2015/0245667 A1 | 9/2015 | Memari et al. |
| 2015/0245668 A1 | 9/2015 | Memari et al. |
| 2015/0272219 A1 | 10/2015 | Hatrick et al. |
| 2015/0359266 A1 | 12/2015 | Memari et al. |
| 2015/0374035 A1 | 12/2015 | Sanchez et al. |
| 2016/0007648 A1 | 1/2016 | Sutton et al. |
| 2016/0007649 A1 | 1/2016 | Sampson et al. |
| 2016/0206005 A1 | 7/2016 | Yamada et al. |
| 2016/0295922 A1 | 10/2016 | John et al. |
| 2016/0324216 A1 | 11/2016 | Li et al. |
| 2016/0331034 A1 | 11/2016 | Cameron |
| 2016/0345632 A1 | 12/2016 | Lipowicz |
| 2017/0055575 A1 | 3/2017 | Wilke et al. |
| 2017/0055580 A1 | 3/2017 | Blandino et al. |
| 2017/0055581 A1 | 3/2017 | Wilke et al. |
| 2017/0055582 A1 | 3/2017 | Blandino et al. |
| 2017/0055583 A1 | 3/2017 | Blandino et al. |
| 2017/0055584 A1 | 3/2017 | Blandino et al. |
| 2017/0071251 A1 | 3/2017 | Goch |
| 2017/0238611 A1 | 8/2017 | Buchberger |
| 2017/0245553 A1 | 8/2017 | Reevell |
| 2017/0251723 A1 | 9/2017 | Kobal et al. |
| 2017/0347706 A1 | 12/2017 | Aoun et al. |
| 2018/0007966 A1 | 1/2018 | Li et al. |
| 2018/0027882 A1 | 2/2018 | Hepworth et al. |
| 2018/0279678 A1 | 10/2018 | Hepworth et al. |
| 2018/0360122 A1 | 12/2018 | Aoun et al. |
| 2019/0098930 A1 | 4/2019 | Fallon et al. |
| 2019/0124978 A1 | 5/2019 | Liu |
| 2019/0125988 A1 | 5/2019 | Trzecieski |
| 2019/0230990 A1 | 8/2019 | Hepworth |
| 2019/0254343 A1 | 8/2019 | Hepworth et al. |
| 2019/0254344 A1 | 8/2019 | Hepworth et al. |
| 2019/0254345 A1 | 8/2019 | Hepworth et al. |
| 2019/0254346 A1 | 8/2019 | Hepworth |
| 2020/0060333 A1 | 2/2020 | Sutton et al. |
| 2020/0367561 A1 | 11/2020 | Yilmaz |
| 2020/0383379 A1 | 12/2020 | Yilmaz |
| 2021/0100284 A1 | 4/2021 | Yilmaz |

FOREIGN PATENT DOCUMENTS

| | | |
|---|---|---|
| AU | 2013214984 A1 | 8/2014 |
| AU | 2013214987 A1 | 8/2014 |
| AU | 2013214991 A1 | 8/2014 |
| AU | 2013214993 A1 | 8/2014 |
| AU | 2013214994 A1 | 8/2014 |
| AU | 2013214997 A1 | 8/2014 |

(56) References Cited

FOREIGN PATENT DOCUMENTS

| | | |
|---|---|---|
| AU | 2013214998 A1 | 8/2014 |
| CA | 2845090 A1 | 2/2013 |
| CA | 2862105 A1 | 8/2013 |
| CA | 2862294 A1 | 8/2013 |
| CA | 2863185 A1 | 8/2013 |
| CA | 2863189 A1 | 8/2013 |
| CA | 2867620 A1 | 8/2013 |
| CA | 2867624 A1 | 8/2013 |
| CA | 2868313 A1 | 8/2013 |
| CN | 2262810 Y | 9/1997 |
| CN | 2686350 Y | 3/2005 |
| CN | 2760984 Y | 3/2006 |
| CN | 101141892 A | 3/2008 |
| CN | 201108029 Y | 9/2008 |
| CN | 101277621 A | 10/2008 |
| CN | 201238609 Y | 5/2009 |
| CN | 101951796 A | 1/2011 |
| CN | 102258219 A | 11/2011 |
| CN | 102595943 A | 7/2012 |
| CN | 102781266 A | 11/2012 |
| CN | 103263083 | 8/2013 |
| CN | 203369383 U | 1/2014 |
| CN | 203369386 | 1/2014 |
| CN | 203801735 U | 9/2014 |
| CN | 2038010735 | 9/2014 |
| CN | 104146352 | 11/2014 |
| CN | 104219973 A | 12/2014 |
| CN | 104244749 A | 12/2014 |
| CN | 104244750 A | 12/2014 |
| CN | 104284606 A | 1/2015 |
| CN | 104287098 A | 1/2015 |
| CN | 104302197 A | 1/2015 |
| CN | 204104830 U | 1/2015 |
| CN | 104394722 A | 3/2015 |
| CN | 204191582 U | 3/2015 |
| CN | 204275207 U | 4/2015 |
| CN | 104661544 A | 5/2015 |
| CN | 204560971 U | 8/2015 |
| CN | 104968225 A | 10/2015 |
| CN | 204812043 U | 12/2015 |
| CN | 204812045 U | 12/2015 |
| CN | 204812046 U | 12/2015 |
| CN | 204812048 U | 12/2015 |
| CN | 204812049 U | 12/2015 |
| CN | 204888735 U | 12/2015 |
| CN | 103859605 | 6/2016 |
| CN | 105852229 A | 8/2016 |
| CN | 205492620 U | 8/2016 |
| CN | 106490692 A | 3/2017 |
| DE | 2548019 A1 | 5/1976 |
| DE | 3938634 A1 | 6/1990 |
| DE | 19645563 A1 | 5/1998 |
| DE | 102005016415 A1 | 11/2006 |
| EA | 201290586 A1 | 12/2012 |
| EA | 201490448 A1 | 12/2014 |
| EP | 0305788 A1 | 3/1989 |
| EP | 0317154 A1 | 5/1989 |
| EP | 0336458 | 10/1989 |
| EP | 0430559 A2 | 6/1991 |
| EP | 0653898 A2 | 5/1995 |
| EP | 0914021 A2 | 5/1999 |
| EP | 1609376 A1 | 12/2005 |
| EP | 1555899 B1 | 12/2006 |
| EP | 1859694 A1 | 11/2007 |
| EP | 2083643 A1 | 8/2009 |
| EP | 2316286 A1 | 5/2011 |
| EP | 2327318 A1 | 6/2011 |
| EP | 2468117 A1 | 6/2012 |
| EP | 2723429 A1 | 4/2014 |
| EP | 2727619 A2 | 5/2014 |
| EP | 2740506 A1 | 6/2014 |
| EP | 2740507 A1 | 6/2014 |
| EP | 2740508 A1 | 6/2014 |
| EP | 2727619 A3 | 7/2014 |
| EP | 2756859 A1 | 7/2014 |
| EP | 2756860 A1 | 7/2014 |
| EP | 2809180 A1 | 12/2014 |
| EP | 2809182 A2 | 12/2014 |
| EP | 2809183 A1 | 12/2014 |
| EP | 2809184 A1 | 12/2014 |
| EP | 2809185 A1 | 12/2014 |
| EP | 2809186 A1 | 12/2014 |
| EP | 2809187 A1 | 12/2014 |
| EP | 2723429 A4 | 4/2015 |
| EP | 2809180 A4 | 7/2015 |
| EP | 2809184 A4 | 7/2015 |
| EP | 2809187 A4 | 7/2015 |
| EP | 2809182 A4 | 8/2015 |
| EP | 2809183 A4 | 8/2015 |
| EP | 2809185 A4 | 8/2015 |
| EP | 2809186 A4 | 9/2015 |
| EP | 2948006 A1 | 12/2015 |
| EP | 2964038 A1 | 1/2016 |
| EP | 2975956 A1 | 1/2016 |
| EP | 2989912 | 3/2016 |
| EP | 3039972 A1 | 7/2016 |
| EP | 3061358 A1 | 8/2016 |
| EP | 3100621 A1 | 12/2016 |
| EP | 3245885 | 11/2017 |
| GB | 607728 A | 9/1948 |
| GB | 2299012 A | 9/1996 |
| GB | 2446440 A | 8/2008 |
| GB | 2504075 A | 1/2014 |
| GB | 2504076 A | 1/2014 |
| GB | 201413018 | 9/2014 |
| GB | 201413019 | 9/2014 |
| GB | 201413021 | 9/2014 |
| GB | 201413025 | 9/2014 |
| GB | 201413027 | 9/2014 |
| GB | 201413028 | 9/2014 |
| GB | 201413030 | 9/2014 |
| GB | 201413032 | 9/2014 |
| GB | 201413034 | 9/2014 |
| GB | 201413036 | 9/2014 |
| GB | 201413037 | 9/2014 |
| GB | 2513061 A | 10/2014 |
| GB | 2523585 A | 9/2015 |
| GB | 2523585 A8 | 9/2015 |
| GB | 2524856 A | 10/2015 |
| GB | 2525080 A | 10/2015 |
| GB | 2525294 A | 10/2015 |
| GB | 2525295 A | 10/2015 |
| GB | 2525480 A | 10/2015 |
| GB | 2525722 A | 11/2015 |
| GB | 2525723 A | 11/2015 |
| GB | 2525724 A | 11/2015 |
| GB | 2525725 A | 11/2015 |
| GB | 2525726 A | 11/2015 |
| GB | 2525727 A | 11/2015 |
| GB | 2529919 A | 3/2016 |
| GB | 2531633 A | 4/2016 |
| HK | 1197203 A1 | 1/2015 |
| HK | 1198138 A1 | 3/2015 |
| HK | 1198142 A1 | 3/2015 |
| HK | 1198143 A1 | 3/2015 |
| HK | 1200128 A1 | 7/2015 |
| HK | 1200129 A1 | 7/2015 |
| HK | 1203128 A1 | 10/2015 |
| IL | 233651 | 8/2014 |
| IL | 233896 | 9/2014 |
| IL | 230930 A | 6/2017 |
| IL | 233851 A | 6/2019 |
| IL | 233653 A | 4/2020 |
| IL | 233885 A | 5/2020 |
| IL | 233894 A | 5/2020 |
| IL | 233895 A | 5/2020 |
| JP | S5736898 U | 2/1982 |
| JP | S6033891 U | 3/1985 |
| JP | S649598 U | 1/1989 |
| JP | H0198470 A | 4/1989 |
| JP | H022331 A | 1/1990 |
| JP | H07192906 A | 7/1995 |
| JP | 3192677 B2 | 7/2001 |
| JP | 3325028 B2 | 9/2002 |

(56) References Cited

FOREIGN PATENT DOCUMENTS

| | | |
|---|---|---|
| JP | 3392138 B2 | 3/2003 |
| JP | 2006503572 A | 2/2006 |
| JP | 2006504431 A | 2/2006 |
| JP | 4324276 B2 | 9/2009 |
| JP | 2009213428 A | 9/2009 |
| JP | 2010506594 A | 3/2010 |
| JP | 2012075370 A | 4/2012 |
| JP | 2012135299 A | 7/2012 |
| JP | 2013509160 A | 3/2013 |
| JP | 2013519384 A | 5/2013 |
| JP | 2014524313 A | 9/2014 |
| JP | 2014532433 A | 12/2014 |
| JP | 2015503335 A | 2/2015 |
| JP | 2015505474 A | 2/2015 |
| JP | 2015505475 A | 2/2015 |
| JP | 2015505476 A | 2/2015 |
| JP | 2015506182 A | 3/2015 |
| JP | 2015508641 A | 3/2015 |
| JP | 2015512617 A | 4/2015 |
| JP | 2015513393 A | 5/2015 |
| JP | 2015513909 A | 5/2015 |
| JP | 2015516809 A | 6/2015 |
| JP | 2016509852 A | 4/2016 |
| JP | 2016517701 A | 6/2016 |
| JP | 2017511703 A | 4/2017 |
| JP | 2017512470 A | 5/2017 |
| KR | 20140070543 A | 6/2014 |
| KR | 20140090138 A | 7/2014 |
| KR | 20140125822 A | 10/2014 |
| KR | 20140125827 A | 10/2014 |
| KR | 20140125828 A | 10/2014 |
| KR | 20140125829 A | 10/2014 |
| KR | 20140127288 A | 11/2014 |
| KR | 20150003845 A | 1/2015 |
| KR | 20150005514 A | 1/2015 |
| KR | 20150018515 A | 2/2015 |
| KR | 20150035488 A | 4/2015 |
| MA | 20150054 A1 | 2/2015 |
| MA | 20150055 A1 | 2/2015 |
| MA | 20150056 A1 | 2/2015 |
| MA | 20150057 A1 | 2/2015 |
| MA | 20150058 A1 | 2/2015 |
| MA | 20150153 A1 | 5/2015 |
| MA | 20150169 A1 | 6/2015 |
| MX | 2014009396 A | 2/2015 |
| MX | 2014009398 A | 2/2015 |
| MX | 2014009393 A | 5/2015 |
| MX | 2014009394 A | 5/2015 |
| MX | 2014009397 A | 5/2015 |
| NZ | 627439 A | 9/2015 |
| NZ | 628058 A | 1/2016 |
| RU | 2015111364 A | 9/2015 |
| RU | 157882 U1 | 12/2015 |
| RU | 2581999 C2 | 4/2016 |
| RU | 2602964 C2 | 11/2016 |
| SG | 2014013627 A | 7/2014 |
| TW | 201315397 A | 4/2013 |
| WO | WO-9406314 A1 | 3/1994 |
| WO | WO-9527412 A1 | 10/1995 |
| WO | WO-02069745 A1 | 9/2002 |
| WO | WO-2004089126 A1 | 10/2004 |
| WO | WO-2006098171 A1 | 9/2006 |
| WO | WO-2007110650 A1 | 10/2007 |
| WO | WO-2009022232 A2 | 2/2009 |
| WO | WO-2010045671 A1 | 4/2010 |
| WO | WO-2011095410 A1 | 8/2011 |
| WO | WO-2011101164 A1 | 8/2011 |
| WO | WO-2012117578 A1 | 9/2012 |
| WO | WO-2012156695 A1 | 11/2012 |
| WO | WO-2013020280 A1 | 2/2013 |
| WO | WO-2013025921 A1 | 2/2013 |
| WO | WO-2013034459 A1 | 3/2013 |
| WO | WO-2013068081 A1 | 5/2013 |
| WO | WO-2013068100 A1 | 5/2013 |
| WO | WO-2013098405 A2 | 7/2013 |
| WO | WO-2013110211 A1 | 8/2013 |
| WO | WO-2013116558 A1 | 8/2013 |
| WO | WO-2013116561 A1 | 8/2013 |
| WO | WO-2013116565 A1 | 8/2013 |
| WO | WO-2013116567 A1 | 8/2013 |
| WO | WO-2013116568 A2 | 8/2013 |
| WO | WO-2013116571 A1 | 8/2013 |
| WO | WO-2013116572 A1 | 8/2013 |
| WO | WO-2013120566 A2 | 8/2013 |
| WO | WO-2013121608 A1 | 8/2013 |
| WO | WO-2013138384 A2 | 9/2013 |
| WO | WO-2013138384 A3 | 10/2013 |
| WO | WO-2013148810 A1 | 10/2013 |
| WO | WO-2013151295 A1 | 10/2013 |
| WO | WO-2013155645 A1 | 10/2013 |
| WO | WO-2013156339 A1 | 10/2013 |
| WO | WO-2013179524 A1 | 12/2013 |
| WO | WO-2014012905 A1 | 1/2014 |
| WO | WO-2014048745 A1 | 4/2014 |
| WO | WO-2014085719 A1 | 6/2014 |
| WO | WO-2014116974 A1 | 7/2014 |
| WO | WO-2014139611 A1 | 9/2014 |
| WO | WO-2014140273 A2 | 9/2014 |
| WO | WO-2014158051 A1 | 10/2014 |
| WO | WO-2013116568 A3 | 11/2014 |
| WO | WO-2014184239 A1 | 11/2014 |
| WO | WO-2015013108 A2 | 1/2015 |
| WO | WO-2015013108 A3 | 4/2015 |
| WO | WO-2015047954 A1 | 4/2015 |
| WO | WO-2015108816 A2 | 7/2015 |
| WO | WO-2015128665 A1 | 9/2015 |
| WO | WO-2015128666 A1 | 9/2015 |
| WO | WO-2015128667 A1 | 9/2015 |
| WO | WO-2016024083 A1 | 2/2016 |
| WO | WO-2016050244 A1 | 4/2016 |
| WO | WO 2016062777 | 4/2016 |
| WO | WO-2016076178 A1 | 5/2016 |
| WO | WO-2016090426 A1 | 6/2016 |
| WO | WO 2016/121143 | 8/2016 |
| WO | WO 2016/135342 | 9/2016 |
| WO | WO-2016178377 A1 | 11/2016 |
| WO | WO-2016208759 A1 | 12/2016 |
| WO | WO-2017055514 A1 | 4/2017 |
| WO | WO-2017149152 A1 | 9/2017 |
| WO | WO-2017160559 A1 | 9/2017 |
| WO | WO 2017/185051 | 10/2017 |
| WO | WO-2019081571 A1 | 5/2019 |

OTHER PUBLICATIONS

Communication pursuant to Article 94(3) EPC for Application No. 1778008.3, dated Sep. 11, 2020, 8 pages.
Communication pursuant to Article 94(3) EPC for Application No. 17835844.6, dated Nov. 25, 2020, 5 pages.
Decision to Grant for Japanese Application No. 2015-559560, dated Apr. 4, 2017, 3 pages (6 pages with translation).
Decision to Grant dated Oct. 22, 2020 for Russian Application No. 2020118485, 9 pages.
Examination Report dated Oct. 26, 2017 for European Application No. 14717683.8, 5 pages.
Extended European Search Report for Application No. 18210216.0, dated May 9, 2019, 8 pages.
Extended European Search Report for Application No. 20210790.0, dated Feb. 18, 2021, 7 pages.
International Preliminary Report on Patentability for Application No. PCT/GB2014/050544, dated Sep. 11, 2015, 6 pages.
International Preliminary Report on Patentability for Application No. PCT/EP2017/073057, dated Mar. 28, 2019, 9 pages.
International Preliminary Report on Patentability for Application No. PCT/EP2017/072811, dated Aug. 20, 2018, 7 pages.
International Preliminary Report on Patentability for Application No. PCT/EP2017/072814, dated Nov. 30, 2018, 8 pages.
International Preliminary Report on Patentability for Application No. PCT/EP2018/083665, dated Mar. 27, 2020, 15 pages.
International Preliminary Report on Patentability for Application No. PCT/GB2014/050545, dated Feb. 27, 2015, 5 pages.

(56) References Cited

OTHER PUBLICATIONS

International Preliminary Report on Patentability for Application No. PCT/EP2017/072813, dated Nov. 30, 2018, 9 pages.
International Preliminary Report on Patentability for Application No. PCT/EP2017/083785, dated Mar. 26, 2019, 17 pages.
International Preliminary Report on Patentability for Application No. PCT/EP2014/055485, dated Oct. 1, 2015, 11 pages.
International Preliminary Report on Patentability for Application No. PCT/EP2017/073061, dated Mar. 28, 2019, 7 pages.
International Preliminary Report on Patentability for Application No. PCT/EP2017/083784, dated Apr. 8, 2019, 23 pages.
International Search Report and Written Opinion for Application No. PCT/EP2014/055485, dated Jul. 31, 2014, 16 pages.
International Search Report and Written Opinion for Application No. PCT/EP2017/072811, dated Dec. 11, 2017, 15 pages.
International Search Report and Written Opinion for Application No. PCT/EP2017/072813, dated Dec. 11, 2017, 12 pages.
International Search Report and Written Opinion for Application No. PCT/EP2017/072814, dated Dec. 11, 2017, 12 pages.
International Search Report and Written Opinion for Application No. PCT/EP2017/073057, dated Feb. 7, 2018, 16 pages.
International Search Report and Written Opinion for Application No. PCT/EP2017/073061, dated Jan. 8, 2018, 13 pages.
International Search Report and Written Opinion for Application No. PCT/EP2017/083784, dated Jun. 20, 2018, 20 pages.
International Search Report and Written Opinion for Application No. PCT/GB2014/050544, dated Sep. 22, 2014, 7 pages.
International Search Report and Written Opinion for Application No. PCT/GB2014/050545, dated Oct. 8, 2014, 9 pages.
International Search Report for Application No. PCT/EP2018/083665, dated Mar. 13, 2019, 5 pages.
International Search Report for Application No. PCT/EP2019/053821, dated May 24, 2019, 3 pages.
International Search Report for Application No. PCT/EP2019/053822, dated May 24, 2019, 3 pages.
Korean Office Action dated Oct. 26, 2020 for Korean Application No. 10-2019-7010642 27 pages.
Korean Office Action dated Oct. 26, 2020 for Korean Application No. 10-2019-7010644, 21 pages.
Notice of Allowance for Japanese Application No. 2015-559560, dated Mar. 27, 2017, 3 pages.
Notice of Reasons for Rejection for Japanese Application No. 2019-535975, dated Jul. 7, 2020, 9 pages.
Notification to Grant Patent Right for Invention of Chinese Application No. 201480023894.4, dated Dec. 4, 2017, 5 pages.
Office Action dated Sep. 30, 2019 for Chinese Application No. 201480017532.4 filed Mar. 19, 2014, 20 pages.
Office Action dated Sep. 8, 2020 for Japanese Application No. 2019-531421, filed Dec. 20, 2017, 16 pages.
Office Action for Chinese Application No. 201480023874.7, dated Mar. 30, 2018, 11 pages.
Office Action for Chinese Application No. 201480023894.4, dated Dec. 8, 2016, 8 pages.
Office Action for Chinese Application No. 2019-531415, dated Oct. 6, 2020, 12 pages.
Office Action for Japanese Application No. 2015-559559, dated Nov. 29, 2016, 4 pages (8 pages with translation).
Office Action for Japanese Application No. 2015-559560, dated Sep. 13, 2016, 4 pages (7 pages with translation).
Office Action for Japanese Application No. 2019-531421, dated Feb. 9, 2021, 14 pages.
Office Action for Japanese Application No. 2020-529231, dated Jul. 20, 2021, 4 pages.
Office Action for Korean Application No. 10-2019-7010649, dated Jan. 19, 2021, 7 pages.
Office Action dated Jan. 11, 2017 for Korean Application No. 10-2015-7025842, 25 pages (67 pages with translation).
Office Action dated Dec. 18, 2018 for Japanese Application No. 2017-172628, 4 pages.
Office Action dated Feb. 19, 2020 for Russian Patent Application No. 2019125438, 21 pages.
Office Action dated Aug. 20, 2020 for Russian Application No. 2019107330, 13 pages.
Office Action dated Jul. 21, 2020 for European Application No. 17780009.1, 7 pages.
Office Action dated Jul. 21, 2020 for Japanese Application No. 2019-513761, 11 pages.
Office Action dated Jul. 21, 2020 for Japanese Application No. 2019-513827, 9 pages.
Office Action dated Jul. 21, 2020 for Japanese Application No. 2019-513842, 11 pages.
Office Action dated Dec. 22, 2020 for Korean Application No. 10-2019-7023118, 20 pages.
Office Action dated Aug. 23, 2016 for Japanese Application No. 2016-503647, 3 pages.
Office Action dated Jul. 7, 2020 for Japanese Application No. JP2019-513828, 12 pages.
Search report dated Sep. 23, 2019 for Chinese Application No. 201480017532.4 filed Mar. 19, 2014, 2 pages.
Search Report dated Mar. 2, 2018 for Great Britain Application No. GB1615609.3, 4 pages.
Written Opinion for Application No. PCT/EP2019/053821, dated May 24, 2019, 6 pages.
Written Opinion for Application No. PCT/EP2019/053822, dated May 24, 2019, 6 pages.
Ye zonglin., "Household Electric Appliance Introduction," Light Industry Press, Mar. 1983, First Edition, pp. 74-78.
Application and File History for U.S. Appl. No. 16/475,571, filed Jul. 2, 2019, inventor: Yilmaz.
Application and File History for U.S. Appl. No. 15/733,181, filed Jun. 4, 2020, inventor: Yilmaz.

* cited by examiner

AEROSOL GENERATING DEVICE AND ARTICLE

PRIORITY CLAIM

The present application is a National Phase entry of PCT Application No. PCT/EP2017/083785, filed Dec. 20, 2017, which claims priority from GB Patent Application No. 1700620.6, filed Jan. 13, 2017, each of which is hereby fully incorporated herein by reference.

TECHNICAL FIELD

The present disclosure relates to an aerosol generating device and an aerosol generating article.

BACKGROUND

Smoking articles such as cigarettes, cigars and the like burn tobacco during use to create tobacco smoke. Attempts have been made to provide alternatives to these articles that burn tobacco by creating products that release compounds without burning.

Examples of such products are so-called e-cigarette devices. These devices typically contain a liquid which is heated to vaporize the liquid to produce an inhalable vapor and/or aerosol. The liquid may contain nicotine and/or flavorings and/or aerosol-generating substances, such as glycerol. The known e-cigarette devices typically do not contain or use tobacco.

Other examples are heating devices which release compounds by heating, but not burning, the material. The material may be for example tobacco or other non-tobacco products, which may or may not contain nicotine.

SUMMARY

According to a first aspect of the present disclosure there is provided an aerosol generating device for generating a flow of aerosol in use, the aerosol generating device defining a first flow path from an air inlet to an outlet portion, and a second, separate flow path from the or another air inlet to the outlet portion, the aerosol generating device comprising: a container for containing aerosol generating material; a heating element arranged to heat the material to generate, in the first flow path, a flow of aerosol; the or another heating element arranged to heat inlet air from the air inlet or the other air inlet to generate, in the second flow path, a flow of heated air; a receiving portion, in the second flow path, arranged to receive an element for modifying a property of the flow of heated air generated in use flowing therethrough, thereby to generate, in the second flow path, a flow of modified air; wherein the outlet portion is arranged to allow egress of the flow of aerosol generated in use, and the flow of modified air generated in use, for inhalation by a user.

The first flow path and the second flow path may extend substantially parallel to one another.

At least a portion of the first flow path may be defined by the container for containing aerosol generating material.

At least a portion of the second flow path may be defined by the receiving portion.

The heating element arranged to heat inlet air may be different from the heating element arranged to heat said material.

The heating element arranged to heat inlet air may be located in the second flow path.

The aerosol generating device may be arranged to allow a user to control the heating element arranged to heat inlet air independently of the heating element arranged to heat the material.

The aerosol generating device may comprise a power source arranged to power both the heating element arranged to heat inlet air and the heating element arranged to heat said material.

The aerosol generating device may be arranged to allow a user to select between outlet of only one, and both, of the flow of aerosol generated in use, and the flow of modified air generated in use.

The outlet portion may define a mixing region for the flow of aerosol generated in use, and the flow of modified air generated in use, to be mixed before inhalation by a user in use.

The aerosol generating device may comprise a mouthpiece, and the mixing region may be defined at least in part by the mouthpiece.

The aerosol generating device may comprise a body, and an aerosol generating article releasably connected to the body, and the aerosol generating article may comprise the container and the receiving portion.

The aerosol generating article may comprise the heater for heating said material and/or the heating element arranged to heat inlet air.

The heating element arranged to heat inlet air may be housed in the body.

According to a second aspect of the present disclosure, there is provided an aerosol generating article for an aerosol generating device for generating a flow of aerosol by heating an aerosol generating material, the aerosol generating article defining a first flow path from an air inlet or an aerosol inlet to an outlet portion, and a second, separate flow path from the or another air inlet to the outlet portion, wherein the first flow path is for the flow of aerosol generated in use, the aerosol generating article comprising: a receiving portion, in the second flow path, arranged to receive an element for modifying a property of a flow of heated inlet air flowing therethrough in use, thereby to generate, in the second flow path, a flow of modified air; wherein the outlet portion is arranged to allow egress of the flow of aerosol generated in use, and said flow of modified air generated in use, for inhalation by a user.

The aerosol generating article may comprise a container for containing the aerosol generating material.

The aerosol generating article may comprise a heating element for heating the aerosol generating material to generate the flow of aerosol in use.

The heating element may be arranged to heat inlet air from said air inlet to generate, in the second flow path, the flow of heated air.

The aerosol generating article may comprise a second, different heating element, and the second heating element may be arranged to heat inlet air from said air inlet to generate, in the second flow path, the flow of heated air.

The aerosol generating article may be arranged to be releasably connectable to said aerosol generating device.

The aerosol generating article may define a first channel defining at least a portion of the first flow path and may define a second channel defining at least a portion of the second flow path.

The first channel and the second channel may extend substantially parallel to one another along substantially the length of the aerosol generating article.

The air inlet of the first flow path may be different from the air inlet of the second flow path.

The aerosol generating device or aerosol generating article may comprise, in the second flow path, downstream of the receiving portion, a one-way-valve to prevent said aerosol generated in use from entering the second flow path.

The receiving portion may comprise one or more retainers for retaining said element received in the receiving portion in use in the receiving portion.

The receiving portion may be arranged to allow said element to be manually inserted into and/or manually removed from the receiving portion in use.

The flow of heated air generated in use may heat at least an outer portion of said element received in the receiving portion in use to a temperature in the range 30° C. to 150° C., or in the range 40° C. to 120° C.

The element may be received in the receiving portion.

The property may be one or more of an organoleptic property of the heater air, a flavor of the heated air, and a nicotine content of the heated air.

The element may be or comprise tobacco.

The aerosol generating material may be a liquid which when heated is volatilizable to generate said flow of aerosol in use.

According to a third aspect of the present disclosure, there is provided an aerosol generating device for generating a flow of aerosol in use, the aerosol generating device defining a first flow path, and a second, separate flow path, the aerosol generating device comprising: a heating element arranged to heat aerosol generating material to generate, in the first flow path, a flow of aerosol; the or another heating element arranged to heat air to generate, in the second flow path, a flow of heated air; and a receiving portion, in the second flow path, arranged to receive an element for modifying a property of the flow of heated air generated in use flowing therethrough, thereby to generate, in the second flow path, a flow of modified air; wherein the first flow path and the second flow path extend substantially parallel to one another.

DETAILED DESCRIPTION

Figure 1:
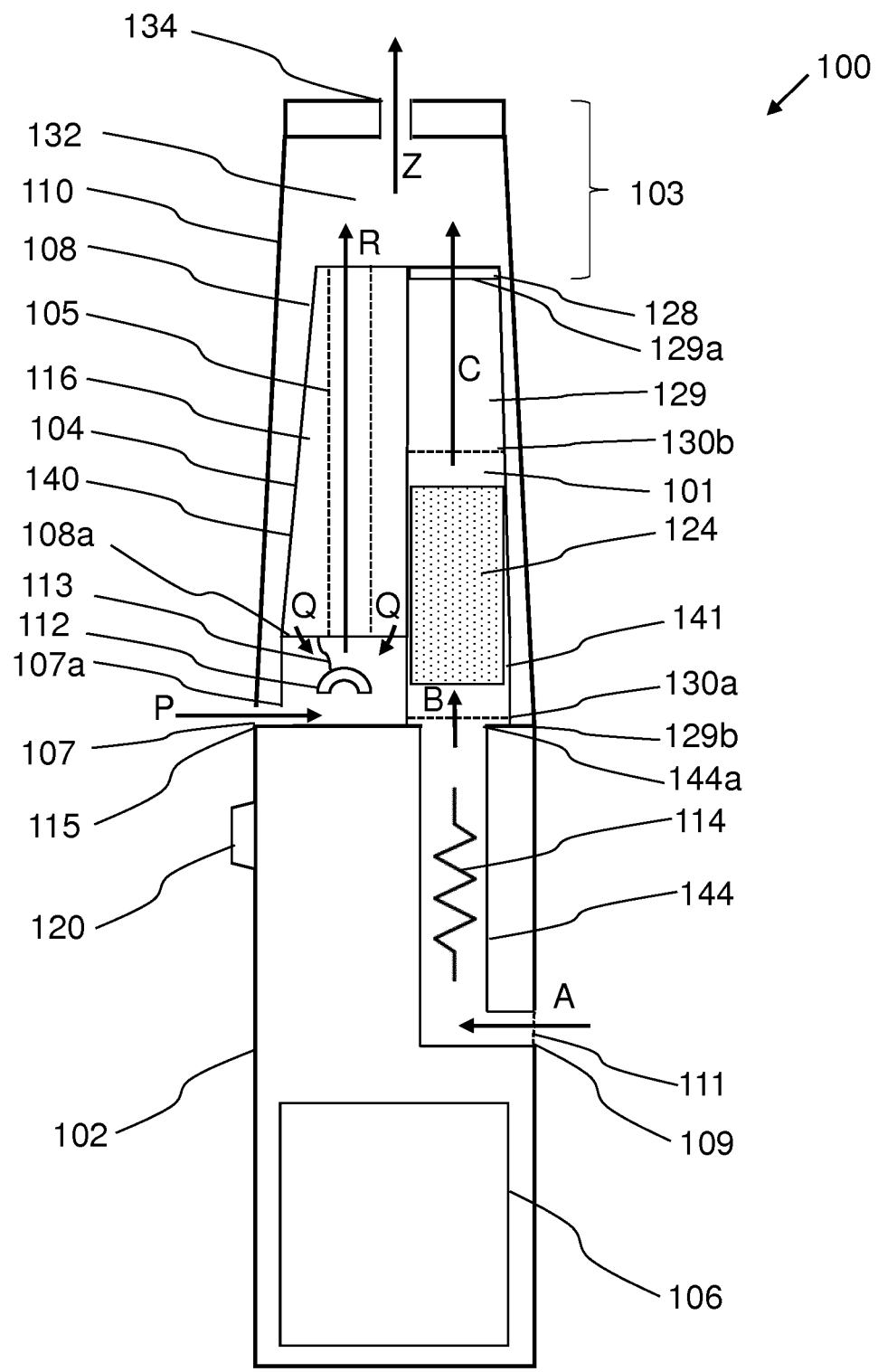
FIG. 1 shows a schematic cross section of a first aerosol generating device, comprising a first aerosol generating article, according to a first example.

Referring to FIG. 1, a schematic of an example aerosol generating device 100 according to a first example is illustrated. The aerosol generating device 100 is an inhalation device (i.e. a user uses it to inhale an aerosol provided by the device). The aerosol generating device 100 is hand-held.

The device 100 comprises a body 102 housing a power source 106 such as a battery 106, and housing a heating element 114 for heating inlet air.

The device 100 comprises an aerosol generating article or cartridge 104 that is removable from the overall device 100. The cartridge 104 may therefore be installed, removed, or replaced in the device 100. The cartridge 104 comprises a connecting portion 115 for releasably connecting the cartridge 104 to the body 102 of the device 100. The cartridge 104 comprises a first portion 140 comprising a liquid container 108 for containing a liquid 116, a wick 113 for drawing the liquid 116 from the liquid container 108, and a heating element 112 for volatilizing the liquid to form a vapor or aerosol. The cartridge 104 comprises a second portion 141 comprising a receiving portion 101. The receiving portion 101 has received therein an element 124 that modifies a property (for example flavor) of heated air passing therethrough.

The device 100 comprises a mouthpiece 110 on which a user can draw. The mouthpiece 110 houses the cartridge 104 and is removeably connected to the body 102 of the device. The mouthpiece defines an outlet 134 for egress of inhalable medium. The mouthpiece 110 may be removed so as to expose the cartridge 104, and hence allow installation, removal and/or replacement of the cartridge 104 from the overall device 100.

The device 100 defines a first flow path (illustrated schematically with arrows P and R) from a first air inlet 107, through the first portion 140 of the cartridge 140, to an outlet portion 103 of the device 100. The device 100 defines a second, separate flow path (illustrated schematically with arrows A to C) from a second air inlet 109 in the body 102 of the device 100, through the second portion 141 of the cartridge 104, to the outlet portion 103 of the device 100.

In broad outline, in the device 100, in the first flow path (P-R) the liquid 116 is volatilized by the first heating element 112 into air from the first air inlet 107 to generate a flow of vapor or aerosol, and in the second, separate flow path (A-C) air from the second air inlet 109 is heated by the second heating element 114, and the heated inlet air flows through the element 124 in the receiving portion 101 that modifies a property of the heated air flowing therethrough. For example, the element 124 may be a flavor element 124 for modifying (imparting) a flavor of (to) the heated air passing therethrough. The first flow path (P-R) and the second flow path (A-C) are combined (Z) downstream of the element 124 at the outlet portion 103, thereby producing an inhalable medium containing vapor or aerosol, as well as air modified (for example flavored) by the element 124.

In this respect, it may be noted that, in general, a vapor is a substance in the gas phase at a temperature lower than its critical temperature, which means that for example the vapor can be condensed to a liquid by increasing its pressure without reducing the temperature. On the other hand, in general, an aerosol is a colloid of fine solid particles or liquid droplets, in air or another gas. A colloid is a substance in which microscopically dispersed insoluble particles are suspended throughout another substance.

For reasons of convenience, as used herein the term aerosol should be taken as encompassing an aerosol, a vapor or a mixture of an aerosol and vapor.

The separation of the first flow path (P-R) and the second flow path (A-C) in the device 100 may prevent aerosol condensing on or in the element 124. This may provide for a consistent delivery of aerosol and/or constituents from the element 124 (for example a consistent taste delivery) over the use of the device 100 and/or the cartridge 104. This may improve user experience. The heating of the inlet air in the second flow path (A-C) that then flows through the element 124 may encourage release of the constituents of the element 124 into the second flow path (A-C), for example, constituents of the element 124 may become entrained in the flow of heated air along the second flow path (A-C). This may provide for a consistent and/or enhanced taste delivery. This may improve user experience. Further, heating of the element 124 by heating inlet air that then flows through the element 124 provides for near instantaneous (or at least faster) heating of the element 124, as compared to heating the element 124 via conduction, for example.

Returning to FIG. 1, the first portion 140 of the cartridge 104 defines a portion of the first flow path (P-R), extending from a first air inlet 107a of the first portion 140 to the outlet portion 103. The second portion 141 of the cartridge 104 defines a portion of the second flow path (B-C), extending from a heated air inlet 129b of the cartridge 104 to the outlet portion 103. The first portion 140 and the second portion 141 of the cartridge 104 may be fluidically separate, but physically connected to one another. For example, the first portion 140 and the second portion 141 may be formed integrally, may be separable and/or removable from one another, or may be glued or otherwise fastened to one another.

The liquid container 108 is elongate and is generally annular in shape. The liquid container 108 defines a first channel 105 running through the liquid container 108 along the length of the liquid container 108. The first channel 105 defines at least a portion of the first flow path (P-R).

The second portion 141 of the cartridge 104 defines a second channel 129 running through the length of the second portion 141, extending from a heated air inlet 129b, to a modified air outlet 129a. The second channel 129 defines at least a portion of the second flow path (A-C). In this example, the receiving portion 101 is defined by a portion of the second channel 129.

The liquid container 108 and/or the receiving portion 101 may be formed of rigid, watertight and airtight materials, such as metal, suitable plastics, etc.

The wick 113 in the first portion 140 of the cartridge 104 is in thermal contact with the heating element 112. The heating element 112 volatilizes the liquid 116 to form an aerosol in the first channel 105. In this example, the first heater 112 and the wick 113 are provided as a single unit, sometimes known as an "atomizer". In this case, where the cartridge 104 includes an atomizer, such a cartridge 104 is often referred to as a "cartomizer" 104. The orientation of the first heater 112 is shown schematically and for example the first heater 112 may be a coil having its longitudinal axis perpendicular or parallel to the longitudinal axis of the cartridge 104. The wick 113 is in contact with the liquid 116. This may be achieved for example by the wick 113 being inserted through a through hole (not shown) in an end wall 108a of the liquid container 108. Alternatively or additionally, the end wall 108a may be a porous member which allows liquid to pass through from the liquid container 108, and the wick 113 may be in contact with the porous end wall 108a. The end wall 108a may be for example in the form of a porous ceramic disk. A porous end wall 108a of this type helps to regulate the flow of liquid onto the wick 113. The wick 113 is generally absorbent and acts to draw in liquid 116 from the liquid container 108 by capillary action (shown in FIG. 1 by arrows Q). The wick 113 can be non-woven and may be for example a cotton or wool material or the like, or a synthetic material, including for example polyester, nylon, viscose, polypropylene or the like, or a ceramic material.

The cartridge 104 is (electrically) connected to the battery 106 in the body 102 of the device 100 to enable the first heating element 112 to be powered. When the first heating element 112 is powered (which may be instigated for example by the user operating a button 120 of the device 100 or by a puff detector (not shown) of the overall device 100, as is known per se), liquid 116 is drawn (shown in FIG. 1 by arrows Q) in from the liquid container 108 by the wick 113 and is heated by the first heating element 112 to volatilize or vaporize the liquid, so as to generate an aerosol in the first flow path (P-R).

Referring again to the first flow path (P-R), as the user draws on the mouthpiece 110, air is drawn through the first air inlet 107 of the device 100, and through the first air inlet 107a of the cartridge 104 (shown in FIG. 1 by arrow P). The liquid 116 is volatilized or vaporized by the heater 112 into the air from the first air inlets 107, 107a thereby to produce a flow of aerosol in the first flow path (P-R). The flow of aerosol is drawn through the channel 105 of the liquid container 108 (shown by arrow R in FIG. 1). The flow of aerosol is drawn out of the channel 105 and into a mixing region 132 defined between the mouthpiece 110 and the cartridge 104. As explained below, the flow of aerosol is mixed in the mixing region 132 with modified air, and drawn out of the device 100 via an aperture or outlet 134 in the mouthpiece 110 of the device, for inhalation by a user (shown in FIG. 1 by arrow Z).

The second heating element 114 (for heating inlet air) is housed in a channel 144 defined by the body 102 of the device 100, the channel 144 extending from the second air inlet 109 of the body 102 of the device 100 to a heated air outlet 144a of the body 102 of the device 100. The channel 144 defines a portion of the second flow path (A-C).

The second heating element 114 is (electrically) connected to the battery 106 to allow the second heating element 114 to be powered. In this example, therefore, the battery 106 is arranged to power both the second heating element 114 (arranged to heat inlet air) and the first heating element 112 (arranged to volatilize the liquid 116). The second heating element 114 may be controlled to be powered, for example, by a user pressing the or another button or interface 120 of the body 102 of the device 100, or by a puff detector (not shown) of the overall device 100, for example. The second heating element 114 heats inlet air from the second air inlet 109 to generate, in the channel 144, a flow of heated air.

In this example, the second heating element 114 is located in the channel 144, that is, the second heating element 114 itself partially interrupts the channel 144 such that the inlet air from the second air inlet 109 passes over and around the heating element 114. This may allow effective and/or efficient heating of the inlet air. The second air inlet 109 comprises a mesh or filter element 111 to prevent dust or other particles or objects from being drawn in through the second inlet 109 and hence contacting the second heater 114.

The receiving portion 101 is a portion of the second channel 129 into which the element 124 for modifying a property of air flowing therethrough is received. Inlet air heated by the second heating element 114 housed in the body 102 of the device 100 is drawn, via the heated air outlet 144a of the body 102 of the device 100, into the heated air inlet 129b of the second channel 129, passes through the element 124 received in the receiving portion 101, and exits from the modified air outlet 129a into the mixing region 132 of the outlet portion 103.

The receiving portion 101 comprises one or more retainers 130a, 130b for retaining the element 124 in the receiving portion 101. A first retainer 130a is located in the second channel 129 upstream of the element 124, and a second retainer 130b is located in the second channel downstream of the element. The first retaining element 130a may prevent the element 124 (or a portion thereof) from falling out of the receiving portion 101 and into the body 102 and/or onto the second heating element 114. The second retaining element may prevent the element 124 (or a portion thereof) from falling out of the receiving portion 101 and out of the second channel 128.

The cartridge 104 comprises, in the second channel 129, downstream of the receiving portion 101, a one-way valve 128. The one-way valve 128 is arranged to prevent the aerosol generated in use from entering the second channel 129. The one-way valve 128 is located at the modified air outlet 129a of the second channel 129 of the cartridge. The one-way valve allows the modified air to flow out from the second channel 129 into the mixing region 132, but does not allow aerosol in the mixing region 132 (for example from the first channel 105 of the cartridge 104) to flow into the second channel 129, and hence into the receiving portion 101, and hence into and/or onto the element 124 received in the receiving portion 101. The one-way valve 128 therefore may ensure that aerosol does not condense on or in the element 124. It will be appreciated that the one-way valve 128 is not essential (i.e. is an optional feature) and that in other examples the cartridge 104 does not comprise a one-way valve.

Referring again to the second flow path (A-C), as the user draws on the mouthpiece 110, air is drawn through the second air inlet 109 in the body 102 of the device 100 (shown in FIG. 1 by arrow A) into the channel 144 of the body 102 of the device 100. The inlet air is drawn over the second heating element 114, thereby to produce the flow of heated air. The flow of heated air is drawn, via the heated air outlet 144a of the body 102 of the device 100, through the second air inlet (heated air inlet) 129a of the cartridge 104, through or past the first retaining element 130a, and into the channel 129 defined by the cartridge (shown in FIG. 1 by arrow B). The flow of heated air is drawn through the element 124 received in the receiving portion 101, and a property of the heated air is thereby modified (for example, as discussed above, the element may impart a flavor to the heated air). The modified air is drawn through or past the second retaining element 130b, through the one-way valve 128, out of the channel 129 via the modified air outlet 129b of the cartridge 104, and into the mixing region 132 in the outlet portion 103 defined between the mouthpiece 110 and the cartridge 104 (shown in FIG. 1 by arrow C). The flow of modified air is mixed in the mixing region 132 with the flow of aerosol exiting the channel 105 of the liquid container 108. The mixture of modified air and aerosol is drawn out of the device 100 via an aperture or outlet 134 in the mouthpiece 110 of the device, for inhalation by a user (shown in FIG. 1 by arrow Z).

The device 100 therefore produces an inhalable medium comprising an aerosol and having properties deriving from the element 114, but without the aerosol having come into contact with the element 114. The device 100 therefore produces such an inhalable medium without the element 114 being altered or degraded by having aerosol condensed in or on it during use. This may improve the consistency of the delivery of inhalable medium over the use of the device 100 and/or the cartridge 104, and therefore may improve user experience.

The second heating element 114 being housed in the body 102 of the device (rather than, for example, in the cartridge 104) may reduce the production cost of the cartridge 104, which may, for example, be disposable. This also may allow a larger and/or more powerful heating element 114 to be used which may heat inlet air faster and/or to a higher temperature and hence release more constituents (and or release constituents more quickly) from the element 124. This may improve user experience.

The modified air and the aerosol being mixed in the mixing region 132 before inhalation by a user may allow for delivery of a uniform and/or homogenous inhalable medium to the user. This may improve user experience. The mixing region 132 being defined between the mouthpiece 110 and the cartridge 104 provides a particularly space efficient mixing region 132. This may reduce the size and/or the production cost of the device 100.

The device 100 and/or cartridge 104 may be arranged such that in use the flow of heated air generated by the second heater 114 heats at least an outer portion of the element 124 received in the receiving portion 101 to a temperature in the range 30° C. to 150° C., for example in the range 40° C. to 120° C. These temperatures may encourage the release of constituents of the element 124 into the air flow, but may not combust the element. This may allow for an enhanced and/or consistent delivery of the modified air component of the inhalable medium by the device 100. These temperature ranges are examples, and it will be appreciated that any increase in temperature of the element 124 above an ambient temperature may encourage release of constituents from the element 124.

In this example, the first flow path (P-R) and the second flow path (A-C) extend substantially parallel to one another along a length of the device 100. The cartridge 104 is elongate, and extends along a length of the device 100. The first portion 140 and the second portion 141 of the cartridge 104 extend side by side along the length of the cartridge (and hence along a length of the device 100). The first channel 105 defined by the liquid container 108 of the first portion 140, and the second channel 109 defined by the second portion 140, extend substantially parallel to one another along a length of the cartridge 104 (and hence substantially parallel to one another along a length of the device 100). This arrangement is space efficient. This may reduce the size and production cost of the cartridge 104 and/or the device 100.

The device 100 may be arranged to allow a user to control the second heating element 114 (arranged to heat inlet air) independently of the first heating element 112 (arranged to volatilize the liquid 116). For example, the button or interface 120 of the body 102 of the device 100 may be arranged to allow a user to set a setting of the second heater 114. For example, this setting may correspond to the current running through the second heating element 114, and hence in turn to a temperature of the heated inlet air and hence in turn to a temperature of the element 124. The settings may range, for example, from an "off" setting in which the second heating element 114 does not heat inlet air, to a "maximum" setting corresponding to a predetermined maximum heating of inlet air by the second heating element 114, and/or any other intermediate setting. This control may allow a user to customize the properties of the inhalable medium exiting the device 100, and hence provide for flexibility in controlling delivery of the inhalable medium. For example, the "off" setting may be selected when the user does not wish the inhalable medium to comprise air modified by the element 124, or to save battery, for example. This provides for a flexible inhalable medium delivery, and hence may improve user experience. The predetermined "maximum" setting may help ensure that inhalable medium exiting the device 100 does not exceed a predetermined temperature, for example. This may ensure safe delivery of the inhalable medium. Alternatively or additionally a "boost" setting or button may be provided to allow a user to initiate or increase heating of inlet air (and hence initiate or increase a release of constituents from the element 124) for a user specified or predetermined period of time. A user may thereby temporarily "boost" a flavor of the inhalable medium produced by the device 100, for example. Similar control and settings may be provided for the first heating element 112. This independent control allows a user more flexibility to control the properties and/or composition of the inhalable medium produced by the device 100, and therefore may improve user experience.

The device 100 may be arranged to allow a user to select between outlet of only one, neither, or both, of the flow of aerosol generated in use, and the flow of modified air generated in use. For example, as mentioned above, the button or interface 120 (which may be an array of buttons, or a user interface, and/or may be controllable remotely for example via a smartphone for example) may be operable to independently control the first heater 112 and the second heater 114. For example, the button 120 may be operable to control circuitry in the device 100 to control that both the first heater 112 and the second heater 114 are off, or one of the first heater 112 and the second heater 114 is on, and the other is off, or both the first heater 112 and the second heater 114 are on, for example. Alternatively or additionally, the device 100 or cartridge 104 may comprise a shutter (not shown) operable to prevent (i.e. physically block) neither, one, or both of the first flow path (P-R) and the second flow path (A-C). For example, the cartridge 104 may comprise a shutter (not shown) operable to block neither, one, or both of the channel 105 defining a portion of the first flow path (P-R) and the channel 129 defining a portion of the second flow path (A-C). This control may allow a user flexibility to control the properties and/or composition of the inhalable medium produced by the device 100, and therefore may improve user experience.

The receiving portion 101 of the cartridge 104 may be arranged to allow the element 124 to be manually inserted into and/or manually removed from the receiving portion 101 in use. For example, the second portion 141 of the cartridge may comprise a closable opening, to allow access to the receiving portion 101, and hence to the element 124 received therein. For example, the one-way valve 128 and the second retaining element 130b may be removable (or not present) to allow access to the receiving portion 101. As another example, the second portion 141 of the cartridge 104 may comprise a door or hatch or the like in a side wall (not shown) of the second portion 141, allowing access to the receiving portion 101. A user may remove the mouthpiece 110 from the body 102 of the device 100 to expose the cartridge 104, open the closable opening (shown), and remove, insert and/or replace an element 124 into the receiving portion 101. As another example, the first retaining element 130a may be removable (or not present, or included instead in the body 102 of the device 100), hence allowing a user to access the element 124 via the second air inlet 129b of the cartridge 104. A user may remove the mouthpiece 110 from the body 102 of the device 100 to expose the cartridge 104, remove the cartridge 104 from the body 102, and remove, insert and/or replace an element 124 into the receiving portion 101 via the second air inlet 129b of the cartridge 104. This flexibility allows a user to customize the inhalable medium produced by the device 100, and hence may improve user experience. This may allow a user to replace the element 124 at a different rate to the replacement of the cartridge 104 as a whole, which may be useful for example if the element is used or degrades before the liquid 116 is used or degrades. This may improve user experience.

In other examples, the cartridge 104 may be disposable, and the cartridge may be sealed on production and thereby arranged not to allow the element 124 to be manually inserted into and/or manually removed from the receiving portion 101 in use. Similarly, the liquid container 108 may be sealed on production and thereby arranged not to allow the liquid 116 to be replaced. This may reduce production costs of the cartridge 104. This may also help prevent leakage of one or both of the liquid 116 and the element 124 from the cartridge 104, and hence provide for a clean and reliable inhalable medium delivery.

The element 124 may be or comprise material that may be used to impart a flavor (and/or one or more other constituents) to the heated air passing therethrough. In some examples, the one or more constituents of the element 124 may comprise constituents inherent to the material itself. The material may for example consist of or comprise tobacco, for example, cut leaf tobacco or ground tobacco. As the heated air passes through and over the tobacco, the heated air entrains organic and/or other compounds or constituents from the tobacco that lend tobacco its organoleptic properties, thus imparting flavor to the heated air. It will be understood however that materials other than tobacco may be used to impart different flavors (and/or one or more other constituents) to the heated air flow. The element 124 may comprise constituents added to a material of the flavor element 124.

Nicotine may be provided in the liquid 116, may be obtained from the element 124, or any combination of these. Flavorings may be added to the element 124 (whether or not the element 124 is or includes tobacco) and/or to the liquid 116. A material of the element 124 may be a solid material, or be a mixture of solid materials, one or more of each comprising one or more constituents that can be mixed with the heated air. It will be appreciated that the element 124 may comprise one or more other constituents that are not entrained into the heated air passing therethrough. It will also be appreciated that the element 124 may comprise a portion that does not impart any flavor to and/or release any constituents into and/or modify any property of the heated air flow.

The element 124 may be porous, for example so as allow heated air to pass through it. The flavor element 124 may be self-supporting, so as to be easily handled by a user (for example easily inserted and/or removed from the receiving portion 101 where the receiving portion 101 allows for this). For example the element 124 may comprise material wrapped partially or wholly in a wrapper, and/or the element 124 may be supported in a resilient housing, for example a plastic housing (not shown). The element 124 may comprise, for example, a flavored carrier material, such as cellulose acetate or the like. The element 124 may be shaped so as to fit easily and/or tightly into a correspondingly shaped receiving portion 101.

The element 124 may be for modifying a property of the heated inlet air other than (or in addition) to flavor, for example it could comprise a substance for modifying a property of the heated air other than (or in addition) to flavor.

In some examples, the element 124 may comprise a substance that modifies one or more other organoleptic properties of the heated air (e.g. modifying the feel or smell or look of the heated air to the user). In some examples, the element 124 may comprise a substance that modifies the nicotine content of the heater air flow passing therethrough. In some examples, the element 124 may comprise a substance that modifies different combinations of two or more of these or indeed other properties of the aerosol.

In the above examples described with reference to FIG. 1, the first heating element 112 for volatilizing the liquid 116 was located in the cartridge 104 and the second heating element 114 for heating inlet air was located in a channel 144 defined by the body 102 of the device. However, this need not necessarily be the case. In other examples, the second heating element 114 may be located instead in the cartridge 104, for example.

Figure 2:
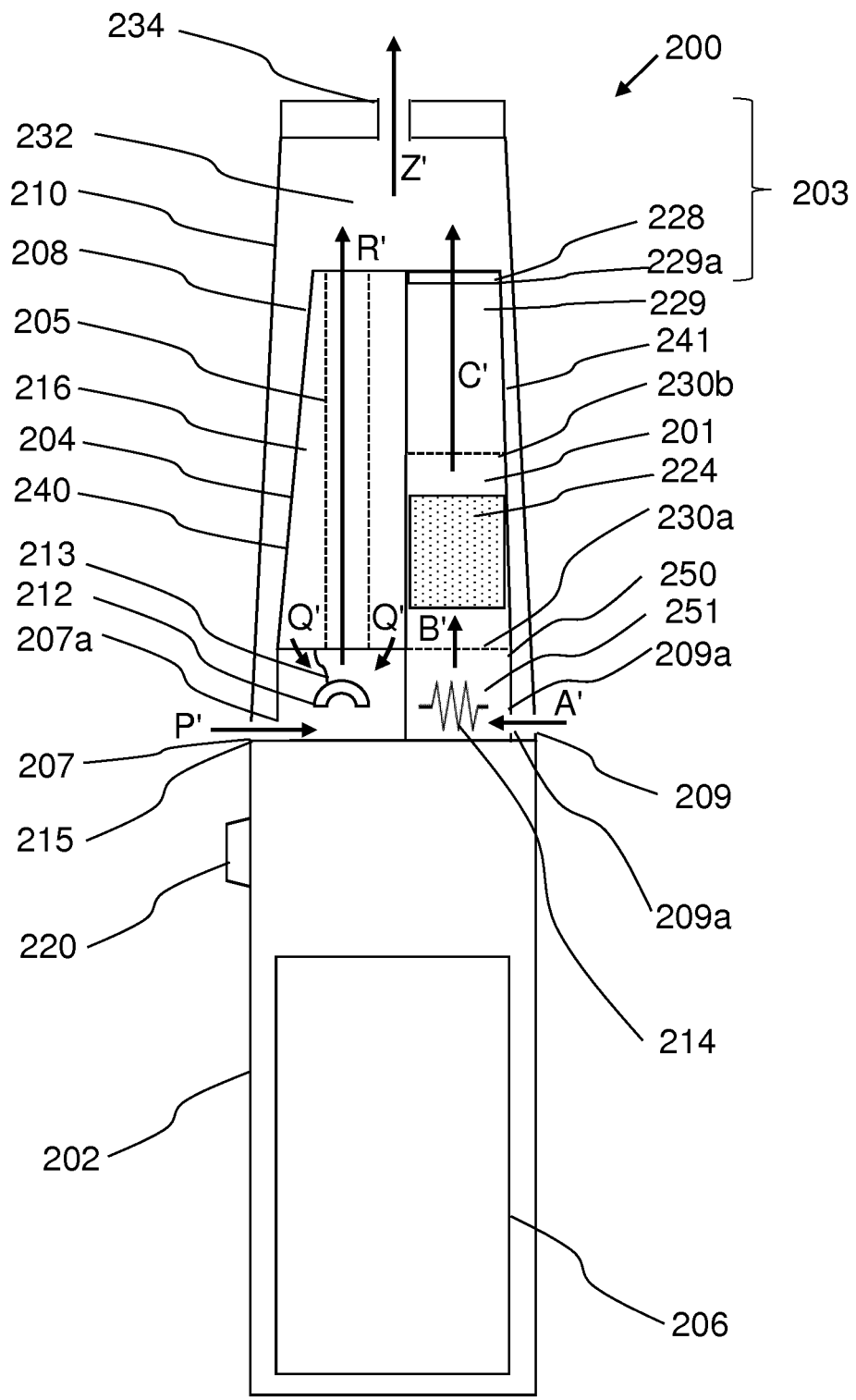
FIG. 2 shows a schematic cross section of a second aerosol generating device, comprising a second aerosol generating article, according to a second example.

FIG. 2 illustrates an aerosol generating device 200, comprising a consumable aerosol generating article or cartridge 204, according to another example. In broad outline, the main difference in this example as compared to the above illustrated in FIG. 1, is that in this example the second heating element 214 for heating inlet air is located in the cartridge 204 rather than in the body 202 of the device. For brevity, features in FIG. 2 and the functioning thereof that are the same or similar to those features already described with reference to FIG. 1 are given similar reference numerals to as in FIG. 1 but increased by 100, and will not be described again.

Referring now to FIG. 2, the second heating element 214 for heating inlet air in the second flow path (A'-C') is housed in a heating portion 250 of the second portion 241 of the cartridge 204. The heating portion 250 defines a heating channel 251 in which the second heating element 214 is located. The heating channel 251 defines a portion of the second channel 229 of the cartridge 204, and extends from the second air inlet 209a of the cartridge 204 to the receiving portion 201. Connecting the cartridge 204 to the body 202 of the device 102 forms an electrical connection (not shown) between the battery 206 and the second heating element 214, thereby allowing the second heating element 214 to be powered. The first heating element 212 and the second heating element 214 may be controlled in a similar way to as described above with reference to FIG. 1, via a button or interface 220 of the device 200 (and/or a puff detector (not shown).

Referring to the first flow path (P'-R'), the aerosol generation in the first flow path (P'-R') is similar to as described above with reference to FIG. 1, and so will not be described again in detail. Suffice to say that, when a user draws on the mouthpiece 210, air is drawn through the first air inlet 207 of the device 200, through the first air inlet 207a of the cartridge 204 (shown in FIG. 2 by arrow P'), and liquid 216 drawn (arrows Q') onto a wick 213 is volatilized or vaporized by the heater 212 into the air to produce a flow of aerosol in the first flow path (P'-R'), which flow of aerosol is drawn through the channel 205 of the liquid container 208 (shown by arrow R' in FIG. 2), and drawn out of the channel 205 and into a mixing region 232 defined between the mouthpiece 210 and the cartridge 204.

Referring to the second flow path (A'-C'), as the user draws on the mouthpiece 210, air is drawn through the second air inlet 209 of the body 202 of the device 100 and through the second air inlet 209a of the cartridge 204 into the heating channel 251 of the cartridge 204 (shown in FIG. 2 by arrow A'). The inlet air is drawn over the second heating element 214 in the heating channel 251, thereby to produce a flow of heated air. The flow of heated air is drawn through or past the first retaining element 230a, and into the receiving portion 201 (shown in FIG. 2 by arrow B'). The flow of heated air is drawn through the element 224 received in the receiving portion 101, and a property (e.g. flavor) of the heated air is thereby modified. The modified air is drawn through or past the second retaining element 230b, through the one-way valve 228, out of the channel 229 via the modified air outlet 229a of the cartridge 204, and into the mixing region 232 defined between the mouthpiece 210 and the cartridge 204 (shown in FIG. 2 by arrow C'). The flow of modified air is mixed in the mixing region 232 of the outlet portion 103 with the flow of aerosol exiting the channel 205 of the liquid container 208. The mixture of modified air and aerosol is drawn out of the device 200 via an aperture or outlet 234 in the mouthpiece 210 of the device, for inhalation by a user (shown in FIG. 2 by arrow Z').

The second heating element 214 being part of the cartridge 204 allows for a simple construction of the body 202 which may reduce production costs. This also allows for the body 202 to be readily compatible for use with other cartridges. The overall device is therefore more flexible. The second heating element 214 being in a (disposable) cartridge may allow a heating element 214 with a relatively short lifetime to be used. This may reduce production costs.

In the above examples, the device 100, 200 comprised a first heating element 112, 212 and a different, second heating element 114, 214. However, this need not necessarily be the case, and in other examples, a single heating element may be used.

Figure 3:
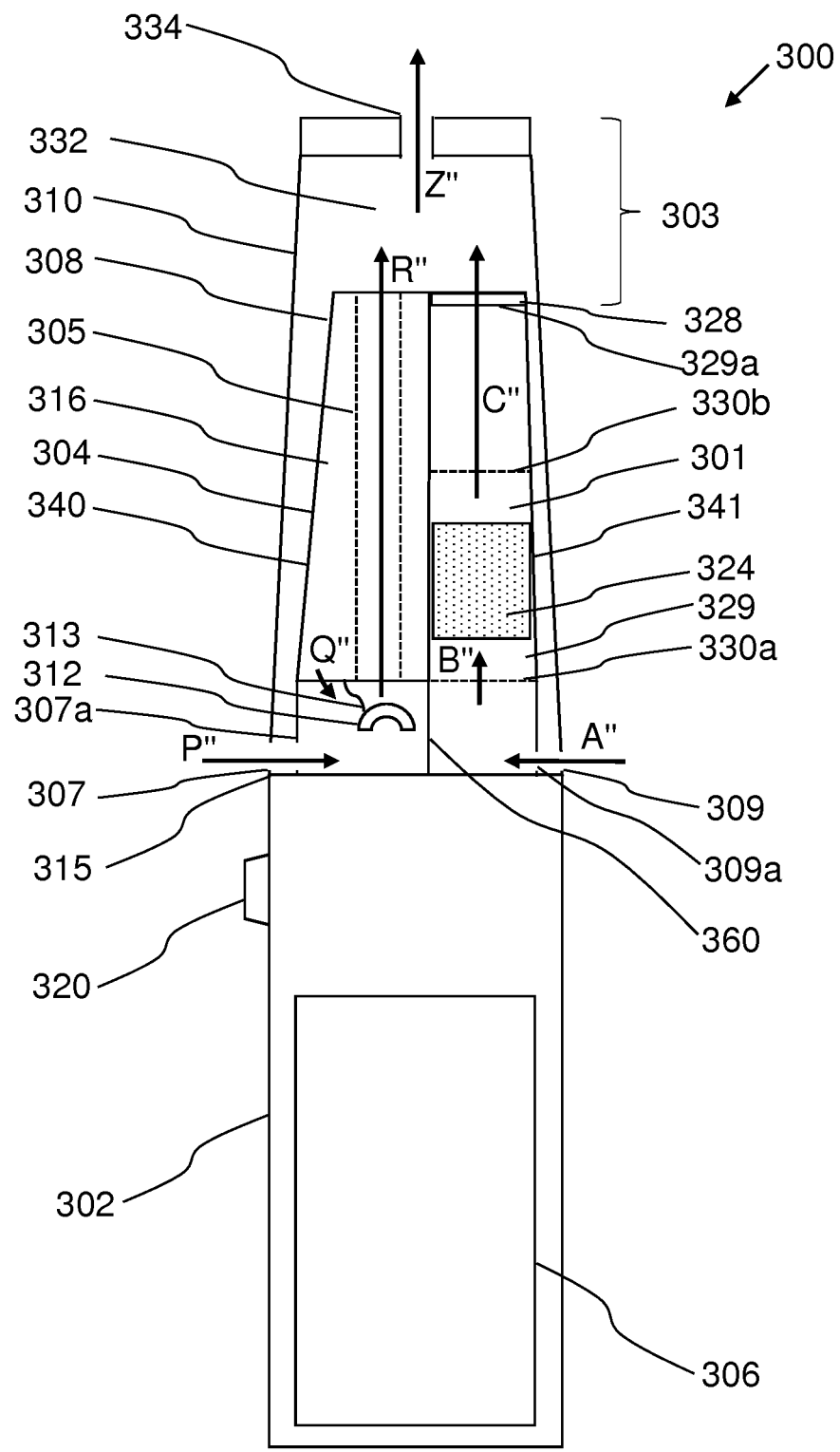
FIG. 3 shows a schematic cross section of a third aerosol generating device, comprising a third aerosol generating article, according to a third example.

FIG. 3 illustrates an aerosol generating device 300 comprising a consumable aerosol generating article or cartridge 304 according to another example. In broad outline, the main difference in this example as compared to the above example illustrated in FIG. 2, is that in this example there is one heating element 260, located in the cartridge 204, both for volatilizing liquid to generate a flow of vapor in the first flow path (P'''-R'''), and for heating inlet air in the second flow path (A''-C'') to produce a flow of heated air. For brevity, features in FIG. 3 and the functioning thereof that are the same or similar to those features already described with reference to FIG. 2 (or indeed FIG. 1) are given similar reference numerals to as in FIG. 2 but increased by 200, and will not be described in detail again.

Referring now to FIG. 3, the cartridge 304 comprises the first heating element 312 arranged to volatilize the liquid 316 to generate, in the first flow path (P''-R''), a flow of aerosol. The heating element 312 is also arranged to heat inlet air from the second air inlet 309 to generate, in the second flow path (A''-C''), a flow of heated air.

The heating element 312 may is located adjacent to (or may be touching, or otherwise in thermal contact with) a dividing wall 360 of the cartridge 104 that separates the first flow path (P''-R'') and the second flow path (A''-C'') at the heating element 312. The dividing wall 360 may be made from or comprise a heat conductor, such as a metal. This may help ensure that the dividing wall 360 is heated to a high enough temperature by the heating element 312 so that inlet air in the second channel 329 is sufficiently heated by passing over or past the dividing wall 360. The dividing wall 360 may have a profiled surface to increase the surface area of the dividing wall 360 thereby to more efficiently transfer heat from the heating element 312 to the inlet air in the second flow path (A''-C''). For example, the dividing wall 360 may comprise one or more heat transfer protrusions (not shown) or "fins" configured as a heat exchanger, for example which protrude into the second flow path (A''-C'') thereby to more efficiently transfer heat from the heating element 312 to the inlet air in the second flow path (A''-C'').

Referring to the first flow path (P''-R''), the aerosol generation in the first flow path (P''-R'') is similar to as described above with reference to FIG. 2, and so will not be described again in detail. Suffice to say that, when a user draws on the mouthpiece 310, air is drawn through the first air inlet 307 of the device 300, through the first air inlet 307a of the cartridge 304 (shown in FIG. 3 by arrow P''), and liquid 316 drawn (arrow Q'') onto a wick 313 is volatilized or vaporized by the heating element 312 into the air to produce a flow of aerosol in the first flow path (P''-R''), which flow of aerosol is drawn through the channel 305 of the liquid container 308 (shown by arrow R" in FIG. 2), and drawn out of the channel 305 and into a mixing region 332 defined between the mouthpiece 310 and the cartridge 304.

Referring to the second flow path (A"-C"), as the user draws on the mouthpiece 310, air is drawn through the second air inlet 309 of the device 300 and through the second air inlet 309a of the cartridge 304 into the second channel 329 of the cartridge 304 (shown in FIG. 3 by arrow A"). The inlet air is drawn over the dividing wall 360 (and/or through or in and around protrusions (not shown) of the dividing wall 360) which is heated by the heating element 312, thereby to produce a flow of heated air. The flow of heated air is drawn through or past the first retaining element 330a, and into the receiving portion 301 (shown in FIG. 3 by arrow B"). The flow of heated air is drawn through the element 324 received in the receiving portion 301, and a property (e.g. flavor) of the heated air is thereby modified. The modified air is drawn through or past the second retaining element 330b, through the one-way valve 328, out of the channel 329 via the modified air outlet 329a of the cartridge 304, and into the mixing region 332 defined between the mouthpiece 310 and the cartridge 304 (shown in FIG. 3 by arrow C"). The flow of modified air is mixed in the mixing region 332 of the outlet portion 303 with the flow of aerosol exiting the channel 305 of the liquid container 308. The mixture of modified air and aerosol is drawn out of the device 300 via an aperture or outlet 334 in the mouthpiece 310 of the device, for inhalation by a user (shown in FIG. 3 by arrow Z").

The heating element 312 being used both to volatilize liquid 316 to produce an aerosol in the first flow path (P"-R") and being used to heat inlet air to generate a flow of heated air in the second flow path (A"-C") may reduce the number of components and/or complexity of the cartridge 304. This may reduce production costs. This may also reduce demand on the power source 306, and hence extend the battery life, for example.

Although in the examples above the first flow path (P-R, etc.) and the second flow path (A-C, etc.) of the device 100, 200, 300 were described as having separate air inlets 107, 109, etc., this need not necessarily be the case, and it will be appreciated that in other examples the first flow path (P-R, etc.) and the second flow path (A-C, etc.) may share a common air inlet (not shown). Similarly, it will be appreciated that in some examples, the portions of the first flow path (P-R) and the second flow path (A-C) defined by the cartridge 104, 204, 304 may share a common air inlet (not shown).

Although the examples above referred to use of a device 100, 200, 300 with a cartridge 104, 204, 304 it will be readily appreciated that there are many configurations of so called e-cigarettes (some of which not having cartridges as such, but rather, for example, refillable liquid containers integral to the device 100) and that the above examples may also be applied to these or other configurations. For example, the first portion 140, 240, etc., comprising the liquid container 108, 208, etc., may be integral to the device 100, 200, etc., and the second portion 141, 241, etc., comprising the receiving portion 101, 201, etc., may be removable from the device, for example. In other examples, the cartridge 104, 204, 304 may be integral to the device 100, 200, 300, and for example the liquid container 108, 208, 308 may be refillable, and the receiving portion 101, 201, 301 may be accessible by a user to remove, insert of replace an element 124, 224, 324 into the receiving portion 101, 201, 301.

In any of the examples described above, a device controller (not shown) may control operation of the device as a whole. Operation of one or more of the heating elements 112, 114, 212, 214, 312 may be controlled so that the liquid 116, 216, 316 and/or material of the element 124, 224, 324 is heated to an optimum temperature. Particular considerations include ensuring that the element 124, 224, 324 does not burn, ensuring that adequate vaporization of the liquid 116, 216, 316 is achieved, and ensuring that inhalable medium produced is at a comfortable and safe temperature for the user. As mentioned above, a puff detector, a device which is known per se, may be provided to signal to the controller when one or more of the heating elements needs to be energized. Alternatively or additionally, the user may control the device via controls or an interface 120, 220, 320, which may be external to the overall device 100, 200, 300, for example via radio control signals, or Bluetooth or the like from a separate control device, such as a smartphone or the like.

In any of the examples described above, the device 100, 200, 300, etc., and/or cartridge 104, 204, 304, etc., may define a first flow path (P-R) and a separate, second flow path (A-C), wherein the first flow path (P-R) and the second flow path (A-C) extend substantially parallel to one another. It will be appreciated that the first flow path (P-R) and the second flow path (A-C) need not necessarily extend parallel to one another along an entire length of the first flow path (P-R) and/or the second flow path (A-C), or along an entire length of the device 100, 200, 300 or cartridge 104, 204, 304, and that a space efficient arrangement can be achieved where the first flow path (P-R) and the second flow path (A-C) extend substantially parallel to one another along a length of the device 100. It will therefore be appreciated that in some examples, the first flow path (P-R) and/or the second flow path (A-C) may comprise portions that do not extend parallel to one another.

Although in the above described examples, the device 100, 200, 300, etc., generates the aerosol by heating a liquid 116, 216, 316, this is not essential and in other examples, the device may generate the aerosol by heating any suitable aerosol generating material, for example heating, but not burning (combusting), an aerosol generating material 116, 216, 316, for example comprising a solid material, that may contain for example tobacco (e.g. a device sometimes referred to as a Tobacco Heating Product (THP) device). In these examples, the liquid container 108, 208, 308 may be alternatively or additionally a container 108, 208, 308 for containing any suitable aerosol generating material 116, 216, 316.

Although in the above described examples, the aerosol generating material 116, 216, 316 (such as the liquid 116, 216, 316) is contained in a container 108, 208, 308 of the cartridge 104, 204, 304, this is not essential and in other examples, the aerosol generating material 116, 216, 316 may be contained, for example in a container in the body 102, 202, 302 of the device 100, 200, 300, or external to the device, 100, 200, 300, for example.

Although in the above described examples, the first heating element 112, 212, 313 for heating the aerosol generating material 116, 216, 316 (such as the liquid 116, 216, 316) to generate an flow of aerosol was part of the cartridge 104, 204, 304, this is not essential and in other examples, the first heating element 112, 212, 312 may be housed in the body 102, 202, 302 of the device 100, 200, 300. For example, the flow of aerosol may be generated in the body 102, 202, 302 of the device 100, 200, 300, and flow through the cartridge 104, 204, 304 in the first flow path (P-R) from an aerosol inlet to an aerosol outlet of the cartridge 104, 204, 304. For example, the first air inlet 107a, 207a, 307a shown in FIGS.

1, 2 and 3 respectively, could be instead in fluid communication with the body 102, 202, 302, and in effect act as an aerosol inlet 107a, 207a, 307a, and the aerosol may then flow through the channel 105, 205, 305 of the cartridge 104, 204, 304, for example.

Accordingly, in some examples, the cartridge 104, 204, 304 may be for a device 100, 200, 300 for generating a flow of aerosol by heating an aerosol generating material 116, 216, 31, the cartridge 104, 204, 304 defining a first flow path (P-R) from an air inlet 107a, 207a, 307a or an aerosol inlet (not shown) to an outlet portion 103, 203, 303, and a second, separate flow path (A-C) from the or another air inlet 109, 209, 309 to the outlet portion 103, 203, 303, the first flow path (P-R) for the flow of aerosol generated in use, the second flow path (A-C) comprising the receiving portion 101, 201, 301 for receiving the element 124, 224, 324 for modifying a property of a flow of heated inlet air flowing therethrough in use.

The liquid 116, 216, etc., in the above examples can be a liquid 116, 216, etc., that is volatilizable at reasonable temperatures, such as in the range of 100-300° C. or more particularly around 150-250° C., as that helps to keep down the power consumption of the device 100, 200, etc., with which the cartridge 104, 204, etc., is used. Suitable materials include those conventionally used in e-cigarette devices, including for example propylene glycol and glycerol (also known as glycerin). Also as described in relation to the examples above, the element 124, 224, etc., may be or comprise a material that may be used to modify a property, such as a flavor, of the heated air passing therethrough. For example, the material may comprise constituents that impart cooling sensations, heating sensations, nutraceutical benefits, stimulating benefits or produce or induce any other sensation or benefit in the user. The material may for example consist of or comprise tobacco. As heated inlet air passes through and over the tobacco material, the air may entrains organic and other compounds or constituents from the tobacco material that lend tobacco its organoleptic properties, thus imparting the flavor to the air as it passes to the mouthpiece. Materials other than tobacco may be used to impart different flavors to the air. For example, materials other than tobacco may be blended with tobacco, or blends of other materials such as, for example, vanilla pods, star anise, mint leaves, other herbs, and the like. For example, flavorants could be included in the material or in the liquid 116, 216, etc., or both. In the example where flavorants are included in both the element 124, 224, etc., and the liquid 116, 216, etc., the generated aerosol may be flavored with a first flavor, and the flavor element 124, 224, etc., may impart a second flavor to the heated inlet air passing therethrough, thereby to generate an inhalable medium having the first and the second flavors. The first flavor and the second flavor may be the same, in which case the element 124, 224, etc., may act so as to enhance the perceived flavor of the inhalable medium. The first flavor and the second flavor may be different, in which case the element 124, 224, 324 may act so as to alter the perceived flavor of the inhalable medium. The user may therefore easily customize the flavor of the inhalable medium exiting the device 100, 200, etc. The element 124, 224, etc., may be a nicotine source that is intended to provide nicotine substantially without any flavor.

The element 124, 224, 324 may be or comprise any tobacco-containing material and may, for example, include one or more of tobacco per se, different varieties of tobacco, tobacco derivatives, pelletized tobacco, extruded tobacco, expanded tobacco, reconstituted tobacco, ground tobacco, tobacco extract, homogenized tobacco or tobacco substitutes. In the case of tobacco, the material may be in the form of a rod of tobacco, a pod or plug of tobacco, loose tobacco, agglomerates, etc., and may be in relatively dry form or in relatively moist form for example. The tobacco may have been modified, for example chemically modified, for example had its pH modified so as to promote the release of selected constituents of the tobacco such as nicotine. Suitable solid materials may include other, non-tobacco, products, which, depending on the product, may or may not contain nicotine. A tobacco rod may be formed using a wrapping material.

As used herein, the terms "flavor" and "flavorant" may refer to materials which, where local regulations permit, may be used to create a desired taste or aroma in a product for adult consumers. They may include extracts (e.g., licorice, *hydrangea*, Japanese white bark *magnolia* leaf, chamomile, fenugreek, clove, menthol, Japanese mint, aniseed, cinnamon, herb, wintergreen, cherry, berry, peach, apple, Drambuie, bourbon, scotch, whiskey, spearmint, peppermint, lavender, *cardamom*, celery, *cascarilla*, nutmeg, sandalwood, bergamot, *geranium*, honey essence, rose oil, vanilla, lemon oil, orange oil, *cassia*, caraway, cognac, jasmine, ylang-ylang, sage, fennel, piment, ginger, *anise*, coriander, coffee, or a mint oil from any species of the genus *Mentha*), flavor enhancers, bitterness receptor site blockers, sensorial receptor site activators or stimulators, sugars and/or sugar substitutes (e.g., sucralose, acesulfame potassium, aspartame, saccharine, cyclamates, lactose, sucrose, glucose, fructose, sorbitol, or mannitol), and other additives such as charcoal, chlorophyll, minerals, botanicals, or breath freshening agents. They may be imitation, synthetic or natural ingredients or blends thereof. They may be in any suitable form, for example, oil, liquid, solid, or powder. For example, a liquid, oil, or other such fluid flavorant may be impregnated in a porous solid material of the element 124, 224, 324 so as to impart flavor and/or other properties to that porous solid material. As such, the liquid or oil is a constituent of the material in which it is impregnated.

The above embodiments are to be understood as illustrative examples of the disclosure.

For example, in some examples, there may be no one-way valve 128, 228, 328 and there may be instead an aperture (not shown) at the modified air outlet 129a, 229a, 329a of the second portion 141, 241, 341 of the cartridge 104, 204, 302. As another example, in some examples, there are no retainers 130a, 130b, 230a, 230b, etc., and the element 134, 234, etc., may be held in the receiving portion 101, 201, 301 for example, via a interference fit, or via contact with a lip (not shown) at either end of the second channel 129, 229, 329, for example. As another example, in some examples, the device 100, 200, 300 may not comprise a mixing region 132, 232, 332, and for example the aerosol and heated inlet air may be delivered to the user as two streams. The cartridge 104, 204, 304 or a portion thereof may itself act as a mouthpiece 110, 210, 310, or an alternative mouthpiece 110, 210, 310 may be provided.

It is to be understood that any feature described in relation to any one example may be used alone, or in combination with other features described, and may also be used in combination with one or more features of any other of the examples, or any combination of any other of the examples. Furthermore, equivalents and modifications not described above may also be employed without departing from the scope of the invention, which is defined in the accompanying claims.

The invention claimed is:

1. An aerosol generating device for generating a flow of aerosol in use, the aerosol generating device defining a first flow path from at least one air inlet to an outlet portion, and a second, separate flow path from the at least one air inlet to the outlet portion, the aerosol generating device comprising:
   a container for containing aerosol generating material;
   at least one heating element arranged to heat the aerosol generating material to generate, in the first flow path, a flow of aerosol the at least one heating element arranged to heat only inlet air from the at least one air inlet to generate, in the second flow path, a flow of heated air; and
   a receiving portion, in the second flow path, arranged to receive an element for modifying a property of the flow of heated air generated in use flowing therethrough, thereby to generate, in the second flow path, a flow of modified air;
   wherein the outlet portion is arranged to allow egress of the flow of aerosol generated in use, and the flow of modified air generated in use, for inhalation by a user.

2. The aerosol generating device according to claim 1, wherein the first flow path and the second flow path extend substantially parallel to one another.

3. The aerosol generating device according to claim 1, wherein at least a portion of the first flow path is defined by the container for containing aerosol generating material.

4. The aerosol generating device according to claim 1, wherein at least a portion of the second flow path is defined by the receiving portion.

5. The aerosol generating device according to claim 1, wherein a first heating element of the at least one heating element is arranged to heat inlet air and is different from a second heating element of the at least one heating element arranged to heat the aerosol generating material.

6. The aerosol generating device according to claim 5, wherein the first heating element is located in the second flow path.

7. The aerosol generating device according to claim 5, wherein the aerosol generating device is arranged to allow a user to control the first heating element independently of the second heating element.

8. The aerosol generating device according to claim 5, further comprising a power source arranged to power both the first heating element and the second heating element.

9. The aerosol generating device according to claim 1, wherein the aerosol generating device is arranged to allow a user to select between egress of only one or both of the flow of aerosol generated in use, and the flow of modified air generated in use.

10. The aerosol generating device according to claim 1, wherein the outlet portion defines a mixing region for the flow of aerosol generated in use, and the flow of modified air generated in use, to be mixed before inhalation by a user in use.

11. The aerosol generating device according to claim 10, wherein the aerosol generating device comprises a mouthpiece, and the mixing region is defined at least in part by the mouthpiece.

12. The aerosol generating device according to claim 1, further comprising a body, and an aerosol generating article releasably connected to the body, and wherein the aerosol generating article comprises the container and the receiving portion.

13. The aerosol generating device according to claim 12, wherein the aerosol generating article comprises one or more of the at least one heating element.

14. The aerosol generating device according to claim 12, wherein the at least one heating element is housed in the body.

15. The aerosol generating device according to claim 1, wherein the air inlet of the first flow path is different from the air inlet of the second flow path.

16. The aerosol generating device according to claim 1, wherein the element is received in the receiving portion.

17. An aerosol generating article for an aerosol generating device for generating a flow of aerosol by heating an aerosol generating material, the aerosol generating article defining a first flow path from at least one air inlet or an aerosol inlet to an outlet portion, and a second, separate flow path from the at least one air inlet to the outlet portion, wherein the first flow path is for the flow of aerosol generated in use, the aerosol generating article comprising:
   a receiving portion, in the second flow path, arranged to receive an element for modifying a property of a flow of only heated inlet air flowing therethrough in use, thereby to generate, in the second flow path, a flow of modified air;
   wherein the outlet portion is arranged to allow egress of the flow of aerosol generated in use, and the flow of modified air generated in use, for inhalation by a user.

18. The aerosol generating device according to claim 16, wherein the property is one or more of an organoleptic property of the heated air, a flavor of the heated air, or a nicotine content of the heated air.

19. The aerosol generating device according to claim 16 wherein the element comprises tobacco.

20. An aerosol generating device for generating a flow of aerosol in use, the aerosol generating device defining a first flow path, and a second, separate flow path, the aerosol generating device comprising:
   at least one heating element arranged to heat aerosol generating material to generate, in the first flow path, a flow of aerosol, the at least one heating element arranged to heat, in the second flow path, only air to generate, in the second flow path, a flow of heated air; and
   a receiving portion, in the second flow path, arranged to receive an element for modifying a property of the flow of heated air generated in use flowing therethrough, thereby to generate, in the second flow path, a flow of modified air;
   wherein the first flow path and the second flow path extend substantially parallel to one another.

* * * * *